United States Patent
Bonnin et al.

(10) Patent No.: US 11,409,137 B2
(45) Date of Patent: Aug. 9, 2022

(54) METHOD AND SYSTEM FOR DETERMINING FITTING PARAMETERS OF AN OPTICAL EQUIPMENT WITH MANUAL IDENTIFICATION

(71) Applicant: Essilor International, Charenton-le-Pont (FR)

(72) Inventors: Thierry Bonnin, Charenton-le-Pont (FR); Marie-Anne Berthezene, Maison-Alfort (FR)

(73) Assignee: Essilor International, Charenton-le-Pont (FR)

( * ) Notice: Subject to any disclaimer, the term of this patent is extended or adjusted under 35 U.S.C. 154(b) by 85 days.

(21) Appl. No.: 16/643,057

(22) PCT Filed: Oct. 9, 2018

(86) PCT No.: PCT/EP2018/077421
§ 371 (c)(1),
(2) Date: Feb. 28, 2020

(87) PCT Pub. No.: WO2019/072815
PCT Pub. Date: Apr. 18, 2019

(65) Prior Publication Data
US 2020/0333635 A1    Oct. 22, 2020

(30) Foreign Application Priority Data
Oct. 11, 2017   (EP) .................................... 17306371

(51) Int. Cl.
*A61B 3/10*     (2006.01)
*G02C 5/00*     (2006.01)
(Continued)

(52) U.S. Cl.
CPC ............ *G02C 13/005* (2013.01); *A61B 3/113* (2013.01); *A61B 3/14* (2013.01)

(58) Field of Classification Search
CPC .......... G02C 13/005; G02C 5/00; G02C 7/02; G02C 7/04; A61B 3/103; A61B 3/14;
(Continued)

(56) References Cited

U.S. PATENT DOCUMENTS

2009/0021693 A1*  1/2009  Sessner ................ G02C 13/003
                                                                351/204
2013/0215379 A1    8/2013  Sayag et al.
(Continued)

FOREIGN PATENT DOCUMENTS

FR      2860887 A1       4/2005
WO   2010/119190 A1    10/2010
WO   2016/075372 A1     5/2016

OTHER PUBLICATIONS

International Search Report, dated Nov. 7, 2018, from corresponding PCT application No. PCT/EP2018/077421.
(Continued)

*Primary Examiner* — Dawayne Pinkney
(74) *Attorney, Agent, or Firm* — Nixon & Vanderhye

(57) ABSTRACT

Disclosed is a method for determining at least one fitting parameter of an optical equipment configured to equip a user, the method including: providing an imaging device; taking a plurality of images of the user equipped with the optical equipment when the user takes successively at least two distinct positions; among the at least two distinct positions, identifying at least one period when the user is in a favorable position to determine the at least one fitting parameter, wherein the at least one period is manually identified by an operator; recording the at least one identified period and at least one image taken during the at least one identified period; determining the fitting parameter on the basis of the at least one recorded image.

20 Claims, 1 Drawing Sheet

(51) Int. Cl.
  *G02C 3/00*    (2006.01)
  *A61B 3/14*    (2006.01)
  *A61B 3/02*    (2006.01)
  *G02C 13/00*   (2006.01)
  *A61B 3/113*   (2006.01)

(58) Field of Classification Search
  CPC ....... A61B 3/152; A61B 3/113; A61B 3/1225;
       A61B 3/024; A61B 3/032; A61B 3/18;
       A61B 3/1015; A61B 3/1005
  USPC ................ 351/204–206, 208–210, 221–223,
       351/245–246, 41, 159.01, 159.73–159.77
  See application file for complete search history.

(56) References Cited

U.S. PATENT DOCUMENTS

| | | |
|---|---|---|
| 2014/0148707 A1 | 5/2014 | Encaoua et al. |
| 2015/0109577 A1* | 4/2015 | Haddadi .................. A61B 3/11 351/204 |
| 2015/0146168 A1 | 5/2015 | Divo et al. |

OTHER PUBLICATIONS

European Search Report, dated Feb. 8, 2018, from corresponding European application No. 17 30 6371.

* cited by examiner

METHOD AND SYSTEM FOR DETERMINING FITTING PARAMETERS OF AN OPTICAL EQUIPMENT WITH MANUAL IDENTIFICATION

BACKGROUND OF THE INVENTION

Field of the Invention

The invention concerns a method and a system for determining at least one fitting parameter of an optical equipment configured to equip a user.

Measuring fitting parameters of an optical equipment consists for instance in locating the pupil of a user equipped with the optical equipment in a favorable position. This favorable position is then checked in different conditions, notably in standing and sitting conditions. It is generally considered that a favorable position corresponds to a natural position of the user in which fitting parameters may be successfully measured. Indeed, measuring fitting parameters when the user is in this favorable position ensures a successful lens fitting, especially for Progressive Power Lenses. However, identifying this favorable position is difficult because it corresponds to a natural position of the user which is specific for each user.

Description of the Related Art

In a traditional method, the optician places the user in a position as close to the favorable position as possible and directly measures fitting parameters on the optical equipment worn by the user. A large drawback of this method is that it is quite difficult for the user to maintain its position along the measurement process so that the accuracy of the measurements is jeopardized. Furthermore, this method is delicate to perform for the optician due to the need of a correct alignment for measurement. A big difference of height between optician and wearer could be an issue for example. Moreover, the constraint induced by the optician giving instructions to the user might jeopardize the possibility for the user to take a natural position.

To ease measuring fitting parameters, automated measuring methods were developed. An example of such automated measuring methods is described in document FR 2 860 887 A1 wherein the user is placed in front of a measuring device comprising a camera. The optician asks the user to make a predetermined move while the camera takes and records images of the user. Particularly, the user is asked to fix a sight while horizontally rotating its head. The measuring device analyses these images and automatically determines the image on which the user is in a favorable position to measure fitting parameters on this image. In an embodiment, the determination of the image is performed by the optician.

The solution provided by FR 2 860 887 A1 is not fully satisfactory because the user is asked to follow predetermined moves which do not allow him to be placed in a natural position. Indeed, when the user is focused on a sight with specific moves to do, the position of the user cannot be really natural and favorable for measuring fitting parameters. Therefore, even if the optician, thanks to his expertise, identifies among the recorded images the one on which the user takes the best position, it will not be necessarily a favorable position. The optician thus cannot be ensured to have favorable images because all images are automatically taken in a predefined process. Furthermore, since the images are automatically taken, even if the optician realizes that none of the taken images is correct to determine fitting parameters, the image acquisition step has thus to be repeated. Consequently, this measurement method does not ensure the optician to have usable images to successfully measure the fitting parameters.

SUMMARY OF THE INVENTION

There is therefore a need to provide a method for determining at least one fitting parameter of an optical equipment configured to equip a user which allows to improve the measurement accuracy and facilitates the optician fitting process.

To solve this problem, the invention provides a method for determining at least one fitting parameter of an optical equipment configured to equip a user, the method comprising:

providing an imaging device;

taking a plurality of images of the user equipped with the optical equipment when the user takes successively at least two distinct positions;

among said at least two distinct positions, identifying at least one period when the user is in a favorable position to determine said at least one fitting parameter, wherein the at least one period is manually identified by an operator;

recording the at least one identified period and at least one image taken during said at least one identified period;

determining said fitting parameter on the basis of said at least one recorded image.

Providing a fitting parameter determining method wherein the operator manually identifies the period during which the user is in a favorable position firstly allows the operator to be fully part of the measuring process. Therefore, the determination of the fitting parameter may be made using the expertise and the experience of the operator from the beginning of the method.

Furthermore, a manual identification also allows to record only specific images that have been already considered as potentially useful. Therefore, the present method allows to ease the measuring process for the operator and the user and reduces image processing with regard to an identifying step performed on images that have been only automatically recorded, such as in document FR 2 860 887 A1. Indeed, recording only images that have been already identified as favorable allows to optimize the measuring process. Furthermore, a rigorous selection of images allows, if needed, an automatic process to get required data.

Furthermore, this method allows the user to participate to the identifying step by giving information to the operator during the identifying step, before recording of the relevant pictures. This is particularly helpful when the user indicates that he is in a favorable position. Thus, the operator can take into account the user's feeling together with his expertise to identify the period during which the user is in a favorable position. Moreover, it might be easier for the user to take a natural position, since the instructions of the operator may be reduced or even completely deleted, in comparison with prior art methods.

According to an embodiment, during the identifying step a plurality of periods are identified to record a plurality of images taken during said plurality of identified periods, the method further comprising a step of selecting at least one image among the plurality of recorded images, said fitting parameter being determined on the basis of said at least one selected image.

According to an embodiment, the operator is the user equipped with the optical equipment.

According to an embodiment, the determining step comprises measuring at least one fitting distance on the at least one recorded image.

According to an embodiment, the at least one fitting parameter is determined on the basis of the at least one fitting distance and reference fitting measurements obtained by statistical analysis.

According to an embodiment, the identifying step is performed either when the user is in a favorable position for a far vision shooting or when the user is in a favorable position for a near vision shooting.

According to an embodiment, the imaging device comprises at least one far vision camera disposed in a room in which the user is photographed, the step of taking a plurality of images comprising taking a plurality of images of the user's face and the optical equipment.

According to an embodiment, the user is free of any movement during the identifying step for a far vision shooting.

According to an embodiment, the user is standing during the identifying step for a far vision shooting.

According to an embodiment, the imaging device further comprises at least one near vision camera configured to take a plurality of images to perform a near vision shooting.

According to an embodiment, the favorable position for a near vision shooting is when the user is in a sitting position, handling and watching toward the at least one near vision camera.

According to an embodiment, the imaging device also comprises another camera disposed on the optical equipment or the user's head, the method further comprising determining the eye gaze direction of the user.

According to an embodiment, the at least one fitting parameter comprises at least one among the pupillary distance, the half pupillary distance, the fitting height, the pantoscopic angle, the far vision point and the near vision point.

According to an embodiment, the optical equipment is eyewear, the at least one fitting parameter allowing to determine lens fitting of said eyewear for the user.

The invention also provides a system for determining at least one fitting parameter of an optical equipment configured to equip a user, the system comprising:
- an imaging device designed to take a plurality of images of the user equipped with the optical equipment when the user takes successively at least two distinct positions;
- means for identifying among said at least two distinct positions at least one period when the user is in a favorable position to determine said at least one fitting parameter;
- a recorder designed to record the at least one identified period and at least one image taken during said at least one identified period;
- determination means designed to determine said fitting parameter on the basis of said at least one recorded image.

The invention is described in more detail below by way of the figures that show only one preferred embodiment of the invention.

DESCRIPTION OF THE PREFERRED EMBODIMENTS

Figure 1:
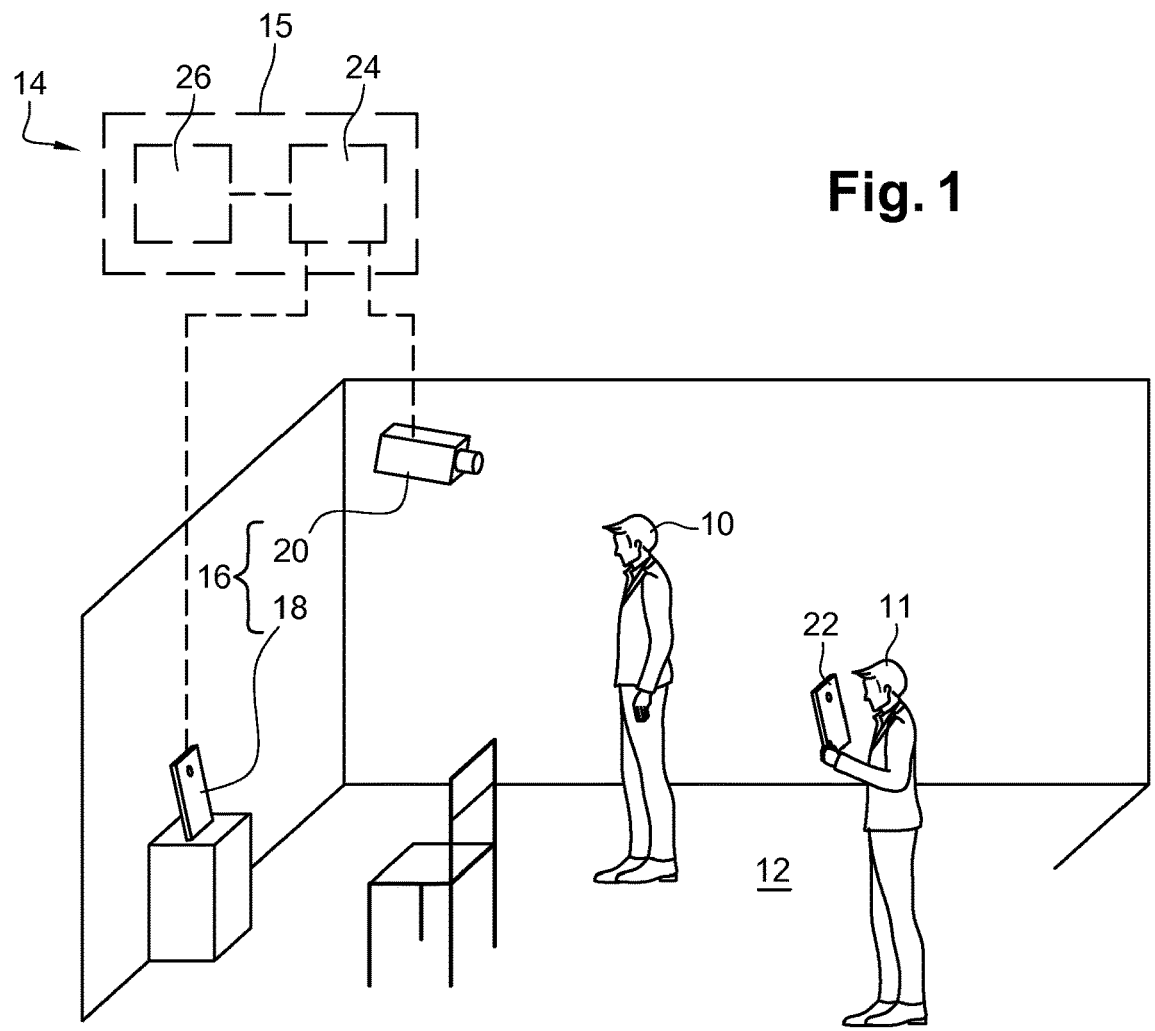
FIG. 1 schematically shows a room provided with a system for determining fitting parameters of an optical equipment worn by a user.

As shown on FIG. 1, a user 10 wearing an optical equipment is positioned in a measuring area 12 of a room. The present invention concerns a method 100 and a system 14 for determining at least one fitting parameter of the optical equipment worn by the user 10.

Said at least one fitting parameter may comprise at least one among the pupillary distance, the half pupillary distance, the fitting height, the pantoscopic angle, the far vision point and the near vision point. The optical equipment is preferably eyewear so that the at least one fitting parameter allows an operator 11, generally an optician, to determine lens fitting of said eyewear for the user 10.

Figure 2:
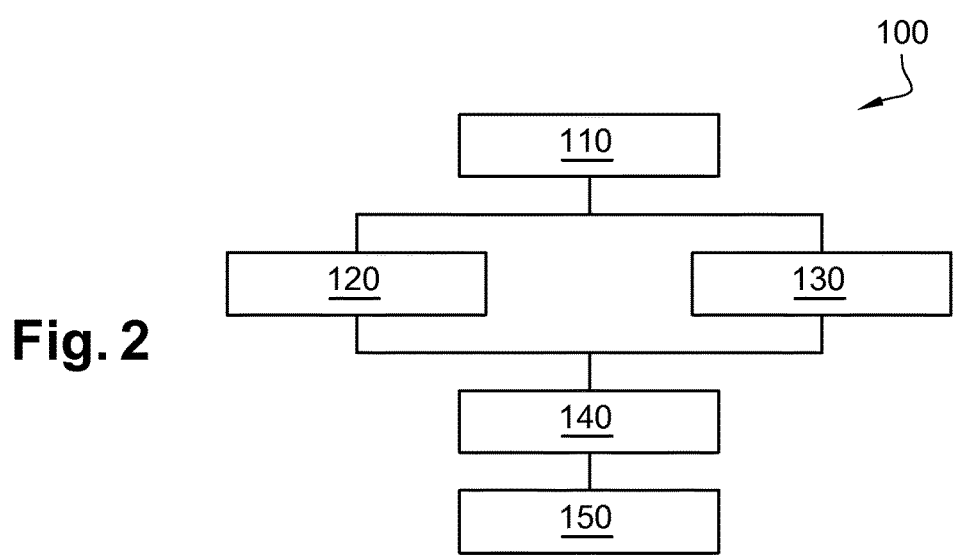
FIG. 2 shows a diagram of a method for determining fitting parameters of an optical equipment worn by a user.

A diagram of such a determining method 100 is shown on FIG. 2.

Determining method 100 first comprises a step of providing 110 an imaging device 16. The imaging device 16 is designed to take a plurality of images of the user 10 equipped with the optical equipment. The imaging device 16 is preferably configured to take images of the user 10 when the user 10 is either in a sitting or standing position. In a preferred embodiment as shown on FIG. 1, the imaging device 16 comprises at least one near vision camera 18 configured to take a plurality of images to perform a near vision shooting. The imaging device 16 preferably also comprises at least one far vision camera 20 configured to take a plurality of images of the user's face and the optical equipment to perform a far vision shooting. Near 18 and far 20 vision cameras are preferably disposed in the room where the user is photographed but not necessary in the measuring area 12 where the user is positioned. Indeed, to make the user more natural during the determining method 100, the near 18 and far 20 vision cameras may be hidden or disposed in a position where the user cannot see them.

Then, a step of taking 120 a plurality of images of the user 10 equipped with the optical equipment when the user takes successively different positions is provided. In other words, images of the user 10 are taken when the user is moving. We mean by "distinct positions", two successive positions wherein the position of at least a part of the user's body has changed. Indeed, the user 10 may take two distinct positions while remaining at the same location in the room. For example, when he is in a sitting position, the user 10 takes two distinct positions if he changes the orientation of his head. All images taken during the step of taking images may be simultaneously recorded.

Determining method 100 also comprises a step of identifying 130 among said at least two distinct positions at least one time during which the user 10 is in a favorable position to determine said at least one fitting parameter. We mean by the term "time", a moment or instant or period when the user is in a favorable position or anatomical posture.

An operator 11, for example an optician or an eye care professional, manually identifies the at least one time during which the user 10 is in a favorable position, or natural position. Assessment of whether the user is in a favorable position belongs to the operator 11 that is thus able to identify specific time during which the user is in this favorable position for determining said fitting parameters. The operator 11 may identify a favorable position of the user by considering one or more of the following: if the head posture is close to an average head posture, eye gaze direction stability, absence of blink, checking if the position of the eyewear is correct and checking if the user 10 is not disturbed by any external conditions. The operator 11 decides when the eye gaze direction or posture is correct for accurately determining fitting cross. The fitting cross correct positions correspond to the position of the pupil in the optical equipment/intersection with the eyewear when the user has a natural posture/gaze direction.

The favorable position may also be defined as an anatomical posture of the wearer. The anatomical posture of the wearer's head corresponds to the position of the wearer's head in the space for which the Frankfurt plane of the wearer's head extends in a horizontal plane. The Frankfurt plane corresponds to a plane passing through the inferior margin of the left orbit and the upper margin of each ear canal or external auditory meatus. It is also said that the wearer is then in an orthostatic position, position in which he achieves a minimum of effort. This anatomical posture may be assumed by the wearer in a seating or standing position.

Identifying step 130 may be performed before the step of taking 120 images. In this case, when the operator 11 identifies a time during which the user 10 is in a favorable position, the imaging device 16 is triggered to take images just after the identifying step 130.

Preferably, identifying step 130 is performed simultaneously or in parallel to the step of taking 120 images. In other words, the operator 11 identifies a time during which the user is in a favorable position while images are taken 120. Simultaneous steps of identifying 130 and taking images 120 avoid and reduce a potential offset between the identification and the taking of images.

After the operator 11 has identified said at least one time and images have been taken, determining method 100 comprises a step of recording 140 said at least one identified time and at least one image taken during said at least one identified time. The system 14 comprises a recorder 24 designed to record the at least one identified time and at least one image taken during said at least one identified time. The step of recording 140 said at least one identified time or instant or moment may comprise recording the exact time at which the favorable position has been identified by the operator. Recording the exact time preferably comprises recording timestamping data at the time the operator identifies the favorable position. Therefore, the operator triggers a step of recording timestamping data when he identifies the favorable position. The image taken at that exact time is then recorded for fitting parameters determination purposes.

Then, a step of determining 150 said fitting parameter is performed on the basis of said at least one recorded image. Particularly, the step of determining 150 said fitting parameter comprises measuring at least one fitting distance on the at least one recorded image. The system 14 comprises determination means 26 designed to determine said fitting parameter on the basis of said at least one recorded image.

When determining said fitting parameter, the operator 11 may tag a pupil position on the recorded image when he considers that the position is favorable or correct. To make the fitting parameter more accurate, the central controller 15 may transmit to the operator 11 information for comparing his tag to statistical position of the pupil. In this latter case, said at least one fitting parameter is determined on the basis of the at least one fitting distance and also of reference fitting measurements obtained by statistical analysis to reduce potential imprecision in the determination of the fitting distance and in the identification of the favorable position. In other words, said at least one fitting parameter may be adjusted with external data that are not directly taken from the identified or selected images to improve the accuracy of the fitting parameters.

Alternatively, determining step 150 may comprise an automatic calculation of the fitting parameters on the basis of the recorded images. Consequently, determining step 150 may be done manually, automatically or by a combination of both ways.

Determining method 100 as described above allows the eye-care professional, here called the operator 11, to remain at the heart of process. The operator 11 is thus able to monitor all determining process to ensure a more reliable measurement of the fitting parameters.

The determining method 100 may be performed in different specific positions of the user. Particularly, the identifying step 130 may be performed either when the user is in a favorable position for a far vision shooting or when the user is in a favorable position for a near vision shooting. Preferably, the identifying step 130 comprises far and near vision shootings to allow the operator 11 to determine fitting parameters based on most common positions of the user, i.e. when the user is in a standing position and in a sitting position to read, and most common measurements useful to correctly fit a PAL device. Having multiple situations of shooting helps the operator 11 for determining said fitting parameters. For example, considering a far vision pupil position and a near vision pupil position allows to give data for computing inset and progression length.

In the far vision shooting, the user 10 is in a standing position. Far vision shooting is performed with the far vision camera 20 of the imaging device 16. The user 10 may freely move in the room during the determining method 100. The user 10 is thus free of any movement during the identifying step 130 for the far vision shooting. In other words, the user 10 moves relatively to the at least one far vision camera 20 during the identifying step 130 to identify said at least one time during the relative movement between the user 10 and the at least one far vision camera 20. In doing so, it is easier for the user to adopt a favorable position because the sensation of carrying-out a measurement process is reduced.

According to an embodiment, the system 14 comprises two far vision cameras 20. A first far vision camera 20 is configured to track the wearer's face, while a second far vision camera 20, for example attached to the first one, take enlarged images of the optical equipment with a high resolution.

In the near vision shooting, the user is in a sitting position. Near vision shooting is performed with the near vision camera 18 of the imaging device 16. Particularly, a favorable position for a near vision shooting is preferably when the user is in a sitting position, handling and watching toward the at least one near vision camera 18. The near vision camera takes images of the user's face. In this latter case, the near vision camera 18 is for example integrated in a tablet computer which can be handled by the user during near vision shooting.

The expressions "far vision camera" and "near vision camera" refer respectively to far vision and near vision postures of the user. In other words, a "far vision camera" is a camera having a position and an orientation allowing to capture an exploitable image of the user when he is in a far vision posture, i.e. in a standing position. In the same way, a "near vision camera" is a camera having a position and an orientation allowing to capture an exploitable image of the user when he is in a near vision posture, i.e. in a seating position. An exploitable image refers to an image allowing the operator or a determination device to determine fitting parameters by means of this image.

Preferably, during the identifying step 130, a plurality of times is identified to record a plurality of images taken during said plurality of identified times. In this latter case, determining method 100 further comprises a step of selecting at least one image among the plurality of recorded images, said fitting parameter being determined on the basis of said at least one selected image.

The system 14 may comprise identification means 22 which can be triggered by the operator 11 when he identifies a time during which the user is in a favorable position. Preferably, these identification means 22 are portable to allow the operator to take the position or the location he considers to be the best. More preferably, identification means 22 comprise a screen allowing the operator 11 to see the user so that identifying step 130 is facilitated and so that the operator cannot be seen by the user, so as not to disturb him. The identification means 22 may be a tablet computer connected to a central controller 15 to display images that are/have been taken and data. Preferably connection between the tablet computer and the central controller 15 is wireless. Particularly, all images from the imaging device 16 may be available on the tablet computer to be displayed. Furthermore, identification means 22 may be configured to allow the operator 11 to perform the determining step 150 directly on the tablet computer. In this latter case, the determination means 26 are integrated to the identification means 22, i.e. in the tablet computer. Therefore, identification means 22 may be a remote control allowing the operator 11 to identify a time during which the user is in a favorable position and then measure at least one fitting parameter directly on the screen of the identification means 22.

Furthermore, the imaging device 16 may also comprise another camera disposed on the optical equipment or the user's head. In this case, the determining method 100 further comprises determining the eye gaze direction of the user. The optical equipment may also comprise an inclinometer to help the operator 11 to determine if the taken image is correct. Indeed, the inclinometer is configured to indicate to the operator 11, for example on the identification means 22, inclination of the user's head. The operator 11 is thus able to determine if the inclination of the user's head is correct with regard to the position of the imaging device 16 to have a favorable position of the user 10. Alternatively to a camera positioned on the user's head, the inclination of the user's head may be determined from the far vision camera 20. In addition, it is possible to pre-select only images for which the head inclination is close to an average inclination value, corresponding to a natural head posture. The average inclination value may be determined by averaging a sample of measurements coming from the inclinometer.

In another embodiment, the at least one far vision camera 20 is motorized and remotely controlled by the operator 11. This avoids the operator 11 to be in the view direction of the user when marking the position of the pupil.

System 14 may also comprise an eye tracker referenced to, or in other words attached to, the frame to acquire the line of sight path. For instance, an eye tracker is a device which can be arranged on a camera taking pictures of the eye or infrared beams emission based and reflections analysis. The most common use is the calculation of the pupil position in order to calculate the eyes rotation. Generally the device is attached to the frame and oriented to see the eye (one by eye). This link allows a direct calculation of the intersection between the line of sight and surface of lenses. Such a use of an eye tracker is particularly interesting because of the capacity to be used during "hidden" (when far (or near) cameras are not able to record) movements of the wearer.

In a preferred embodiment, the central controller 15 comprises a housing wherein the recorder 24 and the determination means 26 are located.

Alternatively, the operator 11 is the user 10 equipped with the optical equipment. In other words, determining method 100 may be performed autonomously by the user 10 wearing the optical equipment.

The invention claimed is:

1. Method for determining (100) at least one fitting parameter of an optical equipment configured to equip a user (10), the method comprising:
   providing a system (14) comprising an imaging device (16) and identification means (22);
   taking (110) a plurality of images of the user (10) equipped with the optical equipment when the user takes successively at least two distinct positions, each of said at least two distinct positions belonging to a far vision shooting or each of said at least two distinct positions belonging to a near vision shooting;
   among said at least two distinct positions, identifying (130) when the user (10) is in a favorable position to determine said at least one fitting parameter, the favorable position corresponding to a position of the user in which the user's head posture is close to a predetermined average head posture and the eye gaze direction of the user is stable;
   triggering the identification means (22) when the operator (11) identifies that said user (10) is in a favorable position;
   identifying at least one period when the identification means (22) are triggered;
   recording (140) said at least one period and at least one image taken at the moment when said at least one identified period is identified;
   determining (150) said fitting parameter on the basis of said at least one recorded image.

2. Method (100) according to claim 1, wherein during the identifying step (130) a plurality of periods are identified to record a plurality of images taken during said plurality of identified periods, the method further comprising a step of selecting at least one image among the plurality of recorded images, said fitting parameter being determined on the basis of said at least one selected image.

3. Method according to claim 1, wherein the operator (11) is the user (10) equipped with the optical equipment.

4. Method (100) according to claim 1, wherein the determining step (150) comprises measuring at least one fitting distance on the at least one recorded image.

5. Method (100) according to claim 4, wherein the at least one fitting parameter is determined on the basis of the at least one fitting distance and reference fitting measurements obtained by statistical analysis.

6. Method (100) according to claim 1, wherein the identifying step (130) is performed either when the user (10) is in a favorable position for a far vision shooting or when the user (10) is in a favorable position for a near vision shooting.

7. Method (100) according to claim 6, wherein the imaging device (16) comprises at least one far vision camera (20) disposed in a room in which the user is photographed, the step of taking (110) a plurality of images comprising taking a plurality of images of the user's face and the optical equipment.

8. Method (100) according to claim 7, wherein moves relative to the at least one far vision camera during the identifying step (130) for a far vision shooting.

9. Method (100) according to claim 6, wherein the user is standing during the identifying step for a far vision shooting.

10. Method (100) according to claim 6, wherein the imaging device (16) further comprises at least one near vision camera (18) configured to take a plurality of images to perform a near vision shooting.

11. Method (100) according to claim 10, wherein the favorable position for a near vision shooting is when the user (10) is in a sitting position, handling and watching toward the at least one near vision camera (18).

12. Method (100) according to claim 1, wherein the imaging device also comprises another camera disposed on the optical equipment or the user's head, the method further comprising determining the eye gaze direction of the user (10).

13. Method (100) according to claim 1, wherein the at least one fitting parameter comprises at least one among the pupillary distance, the half pupillary distance, the fitting height, the pantoscopic angle, the far vision point and the near vision point.

14. Method (100) according to claim 1, wherein the optical equipment is eyewear, the at least one fitting parameter allowing to determine lens fitting of said eyewear for the user (10).

15. Method according to claim 2, wherein the operator (11) is the user (10) equipped with the optical equipment.

16. Method (100) according to claim 2, wherein the determining step (150) comprises measuring at least one fitting distance on the at least one recorded image.

17. Method (100) according to claim 3, wherein the determining step (150) comprises measuring at least one fitting distance on the at least one recorded image.

18. Method (100) according to claim 2, wherein the identifying step (130) is performed either when the user (10) is in a favorable position for a far vision shooting or when the user (10) is in a favorable position for a near vision shooting.

19. Method (100) according to claim 3, wherein the identifying step (130) is performed either when the user (10) is in a favorable position for a far vision shooting or when the user (10) is in a favorable position for a near vision shooting.

20. System (14) for determining at least one fitting parameter of an optical equipment configured to equip a user (10), the system (14) comprising:
- an imaging device (16) designed to take a plurality of images of the user equipped with the optical equipment when the user takes successively at least two distinct positions, each of said at least two distinct positions belonging to a far vision shooting or each of said at least two distinct positions belonging to a near vision shooting;
- identification means (22) configured to be triggered when an operator (11) identifies that said user (10) is in a favorable position among said at least two distinct positions and to identify at least one period when the identification means (22) are triggered, the favorable position corresponding to a position of the user in which the user's head posture is close to a predetermined average head posture and the eye gaze direction of the user is stable;
- a recorder (24) designed to record said at least one period and at least one image taken during said at least one identified period;
- determination means (26) designed to determine said fitting parameter on the basis of said at least one recorded image.

* * * * *